United States Patent [19]

Peterson

[11] 4,075,234

[45] Feb. 21, 1978

[54] HYDRATED SOAP MAKING

[75] Inventor: Donald John Peterson, Cincinnati, Ohio

[73] Assignee: The Procter & Gamble Company, Cincinnati, Ohio

[21] Appl. No.: 731,163

[22] Filed: Oct. 12, 1976

[51] Int. Cl.$^2$ .................. C11C 1/04; C11D 13/00; C11C 1/08; C10M 1/24

[52] U.S. Cl. ............................ 260/417; 252/41; 260/540; 260/541; 260/542; 260/515 R

[58] Field of Search ............ 252/41; 260/540, 541, 260/542, 515 R, 417

[56] References Cited

U.S. PATENT DOCUMENTS

| | | | |
|---|---|---|---|
| 2,753,364 | 7/1956 | Boner et al. ........................ | 252/41 |
| 3,133,942 | 5/1964 | Hahl .................................. | 252/441 |
| 3,173,869 | 3/1965 | Watson et al. ..................... | 252/41 |
| 3,242,088 | 3/1966 | Bright et al. ....................... | 252/41 |
| 3,657,146 | 4/1972 | Franisen et al. ................... | 260/417 |

*Primary Examiner*—Delbert E. Gantz
*Assistant Examiner*—Irving Vaughn
*Attorney, Agent, or Firm*—Jerry J. Yetter; Julius P. Filcik; Richard C. Witte

[57] ABSTRACT

Sodium and lithium salts of organic carboxylic acids are prepared by saponifying the corresponding organic carboxylic acid ester with a concentrated aqueous solution of sodium hydroxide or lithium hydroxide in a liquid reaction medium comprising an alkyl nitrile, separating said salts from the reaction mixture, and removing excess alkyl nitrile from the salts.

15 Claims, No Drawings

HYDRATED SOAP MAKING

BACKGROUND OF THE INVENTION

The present invention encompasses methods for saponifying organic acid esters, including fatty acid glyceride esters. More specifically, organic acid esters are saponified using a concentrated aqueous solution of sodium hydroxide or lithium hydroxide in a liquid reaction medium comprising an alkyl nitrile to provide partially solvated, yet solid, filterable sodium or lithium metal salts of the organic acids. When fatty acid esters are used in the process, soaps and lubricating greases are secured.

The preparation of alkali metal salts of organic acids by saponifying the corresponding organic acid esters, as in traditional soap making processes, is typically carried out using an alkali metal hydroxide base, the organic acid ester, and water as the reaction medium. Heretofore, such reactions have been energy intensive for at least two reasons. First, heat energy is required to initiate and sustain the saponification of the organic acid ester by the aqueous solution of the alkali metal hydroxide. Second, the organic acid salts are strongly solvated by the water from the aqueous reaction medium. Accordingly, some of the water must be removed to recover the organic acid salts, and heat energy is needed for this solvent removal step. Moreover, the soaps prepared in water are in a sticky, intractable, non-crystalline state and cannot be recovered by simple filtration processes.

The co-pending application of Peterson, entitled SOAP MAKING, Ser. No. 731,183, filed Oct. 12, 1976, teaches that substantially anhydrous alkyl nitriles provide a reaction medium wherein organic acid esters can be saponified with alkali metal hydroxides to provide the alkali metal salts of organic acids which precipitate from the reaction medium in an unsolvated form. Accordingly, solvent removal is not a high energy consuming step in the disclosed process. Moreover, the Peterson process is exothermic and, once initiated, proceeds substantially to completion without external heating. Soap making processes carried out by the Peterson process using fatty glycerides as the organic acid ester provide substantially dry, unsolvated, crystalline, filterable white soap powder in an extremely short period of time in exceptionally high yields.

It has now been determined that the basic Peterson process for making soap can be modified to employ concentrated aqueous solutions of sodium hydroxide or lithium hydroxide, thereby facilitating handling. Moreover, concentrated solutions of these alkali metal hydroxides are relatively inexpensive articles of commerce, as compared with their solid form. By controlling the total amount of water introduced into the alkyl nitrile medium in the syrupy, concentrated hydroxide solution, solid, yet partially hydrated, filterable white powders comprising the alkali metal salts of fatty acids are still secured.

If excessive amounts of water are used in the present process, the special advantages are lost and the reaction proceeds in much the same manner as wet process soap manufacture, with the formation of viscous masses of the fatty acid salts or soaps at reduced reaction rates. Indeed, with alkali metal hydroxides such as KOH, RbOH and CsOH, intractable, tacky soaps are secured in the presence of even small (greater than about 10%) amounts of water in the total reaction system. Accordingly, preparation of the soaps of these latter alkali metals is preferably carried out via the anhydrous Peterson process, mentioned above, and aqueous solutions of KOH, RbOH or CsOH are not used in the practice of the present invention.

RELATED REFERENCES

The art of preparing the alkali metal salts of organic acids, especially as it is embodied in soap making processes, is old and is the subject of a large body of literature. Anhydrous soap making processes have been disclosed heretofore, as have soap making processes which employ organic solvents as the reaction medium. The alkyl nitriles used as the reaction medium in the present process are well-known materials.

Despite the voluminous literature in this area and the long history of soap making and syntheses of fatty acid salts, the present process does not appear to have been contemplated heretofore.

Acetonitrile (methyl cyanide; cyanomethane; ethanenitrile) is a highly preferred alkyl nitrile solvent for use in the present process. As pointed out in THE MERCK INDEX, Seventh Ed., page 8, this material has been used to extract fatty acids from fish liver oils and other animal and vegetable oils. This material is also known as a medium for producing reactions involving ionization, as a solvent in non-aqueous titrations, and as a non-aqueous solvent for inorganic salts.

The use of acetonitrile as an extraction solvent for separating/removing various materials from compositions containing fatty acids, sterols, and the like, is disclosed in the following references: U.S. Pats. Nos. 2,681,922, Balthis, 6/22/54; 2,528,025, Whyte, 10/31/50; Chemical Abstracts 38,6180; 84,80436u; 48,6698; 57,13224; 47,3660; 60,2330; 49,15266; 54,5126; 50,14322; and 46,6468.

The use of propionitrile in various liquid phase extraction processes involving glycerides, fatty acids, and the like, is disclosed in U.S. Pats. Nos. 2,316,512, Freeman, 4/13/43; 2,200,391, Freeman, 5/14/40; 2,313,636, Freeman, 3/9/43; 2,390,528, Freeman, 12/11/45; and Canadian 488,250, Freeman, 11/18/52.

Processes for manufacturing modified oil products from fatty oils, for manufacturing soap compositions, and for preparing metallic salts of higher fatty acids, which are carried out under anhydrous conditions or with the use of organic solvents of various types are disclosed in the following references: U.S. Pats. Nos. 1,957,437, Auer, 5/8/34; 3,376,327, Freeland, 4/2/68; 2,271,406, Thurman, 1/27/42; 2,383,630, Trent, 8/28/45; 3,476,786, Lally and Cunder, 11/4/69; Chemical Abstracts 53,20838; 26,5875; 52,7743; and 53,20850.

Various miscellaneous references relating to the use of cyano compounds or amines of various types in the preparation of carboxylic acids and general references to the use of acetonitrile as a solvent are as follows: U.S. Pats. Nos. 2,042,729, Ralston and Poole, 6/2/36; 3,828,086, Kenney and Donahue, 8/6/74; 3,519,657, Olah, 7/7/70; 2,211,941, Sullivan, 8/20/40; 1,833,900, Hoyt, 12/1/31; 2,402,566, Milas, 6/25/46; 2,640,823, Gloyer and Vogel, 6/2/53; 2,895,974, Case, 7/21/59; and Chemical Abstracts 53,9642.

German Patentschrift 1,254,139, May 30, 1968, discloses a process for preparing saturated fatty acids by reacting an α-olefin with a stoichiometric excess of acetonitrile, or acetate reagent, in the presence of an organic peroxide.

It is clear that the use of the alkyl nitriles as an extraction/separation medium in the manner suggested by these references does not contemplate their use as a reaction solvent in the manner of the present invention. Moreover, the use of organic solvents, anhydrous conditions, or cyano compounds to prepare soaps, and the like, does not contemplate the present invention.

Attention is specifically directed to U.S. Pat. No. 3,133,942, Hahl, patented May 19, 1964, and U.S. Pat. No. 2,753,364, Boner and Breed, patented July 3, 1956. The '942 patent relates to the production of metal salts of organic acids and, as disclosed therein, is carried out by using an organic acid and certain metals in the form of metal powders. Inert organic solvents, including acetonitrile, propionitrile and benzonitrile, are disclosed for use in the process. The process differs from that of the present invention in that it uses neither alkali metal hydroxides nor organic acid esters as the starting materials. Moreover, many of the solvents disclosed as being useful in the '942 patent are not contemplated for use herein.

The Boner, et al., patent, above, relates to a method for manufacturing lithium soaps (lubricating greases) using lithium carbonate and free fatty acids as the starting materials. Acetonitrile, benzonitrile and "benzyl cyanide" are taught to be useful solvents in the process, along with many other organic solvents. It will be appreciated that this reference does not teach the use of alkali metal hydroxides, nor organic esters, especially glyceride esters, such as those used in the present invention; is almost unlimited as to the type of organic nitrogen-containing materials suggested for use as the solvent medium; and does not teach or suggest the present process which is limited to the alkyl nitriles which have now been discovered to be particularly advantageous when employed in the manner disclosed herein.

Attention is also directed to the review article Khim. Prom. (Moscow) 1968 44 (10) 722–6 (Russ.) which, in abstract form (C.A. 70 28299y), is said to relate to the use of MeCN as a solvent, its reactions with aldehydes, ketones, alcohols, dienes and organic acids, substitution reactions and with inorganic compounds, and which cites 90 references.

Attention is also directed to the review article by E. J. Fischer, Allgem. Oel-u. Fett-Ztg. 33, 78–81 (1936) which, in abstract form (C.A. 30 3539), is said to relate to methods for preparing acetonitrile and its use, principally as a solvent.

The copending applications of Peterson, entitled BASE REACTANT, Ser. No. 731,176, filed Oct. 12, 1976, and ENERGY SAVING DETERGENT MANUFACTURE, Ser. No. 731,182, filed Oct. 12, 1976, all disclosures of which are incorporated herein by reference, relate to the base systems employed herein as well as the end use of the partially hydrated soaps prepared in the manner of this invention.

SUMMARY OF THE INVENTION

The present invention encompasses a process for preparing the sodium and lithium salts of organic acids. The process comprises saponifying the organic ester corresponding to the organic acid salt desired using a concentrated aqueous solution of the corresponding alkali metal hydroxide in a liquid reaction medium comprising an alkyl nitrile compound. The amount of water introduced into the total reaction mixture is controlled to provide filterable, solid, yet partially hydrated organic acid salts. If too much water is employed, the reaction proceeds at a much slower rate, the reaction product is converted from a solid form to a tacky, intractable mass and the overall advantages of the process are lost.

The reaction herein can be carried out using glyceride esters, including the mixed mono-, di- and triglyceride esters derived from animal fats and oils and/or vegetable fats and oils. Such materials typically comprise fatty acid ($C_{10}$–$C_{20}$) esters and are well known for use in soap making processes. Accordingly, the process herein can be used to prepare water-soluble soaps which are, typically, the sodium salts of $C_{10}$–$C_{20}$ organic acids.

The present process can also be carried out using lithium hydroxide and $C_{10}$–$C_{24}$ fatty acid esters, thereby securing lithium "soaps" which are especially useful and known in the art as lubricating greases.

The process herein is simply and economically carried out by admixing the alkyl nitrile reaction medium, the ester, and the concentrated aqueous solution of sodium or lithium hydroxide in a suitable reaction vessel, initiating the reaction (typically by gentle heating) and allowing the reaction to proceed. The reaction is somewhat exothermic and, once initiated, self-sustaining. Heating can be used to increase the yield of organic acid salts.

Soaps prepared by the present process simply precipitate from the reaction medium as partially hydrated, filterable, substantially white powders. Advantageously, much of the colored matter which is commonly present in commercial grades of animal fats and oils which can be used as an inexpensive ester starting material is retained in solution in the alkyl nitrile. Accordingly, an excellent soap product, substantially freed from color bodies, can be secured by the present process. Typical yields of soaps (or lubricants) are in the range of 90% in a matter of a few minutes.

DETAILED DESCRIPTION OF THE INVENTION

The present invention encompasses a process for preparing the sodium and lithium salts of organic acids which comprises saponifying the corresponding organic acid ester with a concentrated aqueous solution of the corresponding metal hydroxide in a liquid reaction medium comprising an alkyl nitrile. The organic acid esters employed herein can be simple alkyl or aryl esters, or can be glyceride esters such as the triglycerides which typically constitute the major proportion of the materials present in fats and oils derived from animal or vegetable sources. The reaction herein can be used, for example, to prepare lubricating greases by saponifying $C_{10}$–$C_{24}$ organic acid esters with lithium hydroxide. The present process can also be employed to prepare water-soluble detersive surfactants, i.e., soap, by saponifying esters of organic acids having chain lengths in the range of about $C_{10}$–$C_{20}$, preferably $C_{12}$–$C_{18}$. The reaction does not appear to depend on the nature of the acid ester used; hence, alkali metal salts of organic acids having chain lengths shorter or longer than mentioned above, as well as branched chain and aryl organic acids, can also be prepared in the manner of this invention.

By "sodium and lithium salts of organic acids" herein is meant compounds of the formula RCOOM, wherein the RCOO- group is an organic acid substituent, unlimited in the type of R group, and wherein M is sodium or lithium.

By "organic acid ester" herein is meant a compound of the formula RCOOR', wherein RCOO— is as above, and wherein group R' is an organic substituent group derived from an alcohol or polyol, unlimited in type.

By "alkyl nitrile" herein is meant a compound of the formula R"CN, wherein R" is a linear, branched chain or cyclic aliphatic substituent. Typical examples of such materials are acetonitrile and propionitrile, which are preferred for use herein. Aromatic nitriles, e.g., benzonitrile, have been found not to be useful as a reaction medium and are not encompassed by the present invention. Acetonitrile is the most highly preferred alkyl nitrile for use herein.

By "glycerides" herein is meant organic acid esters of glycerol. The term "glycerides" encompasses mono-, di- and triglycerides, since glycerol is a trihydric alcohol which can be esterified on any, or all, of the three hydroxyl groups. Triglycerides constitute the major components of naturally-occurring fats and oils which are typically used as starting materials in soap making processes.

By "animal or vegetable fats and oils" herein is meant the organic acid glyceride materials which can be secured from a wide variety of sources. Specific, nonlimiting examples of such materials include lard, tallow, coconut oil, palm oil, various by-products from animal rendering operations, oils from oleaginous seeds such as the soybean, sunflower seeds, and the like, cottonseed oil, etc. Typical listings of such materials are widely available, and all such glyceride mixtures are useful in the present process.

By the term "comprising" herein is meant that various other, compatible ingredients can be present in the reaction medium as long as the critical reactants and alkyl nitrile are present. The term "comprising" thus encompasses and includes the more restrictive terms "consisting of" and "consisting essentially of" which can be used to characterize the essential materials (ester, sodium or lithium hydroxides and alkyl nitrile) used herein.

All percentages herein are by weight, unless otherwise specified.

The process herein is carried out by simply admixing the carboxylic acid ester to be saponified with the alkyl nitrile and a concentrated solution of sodium hydroxide or lithium hydroxide in any suitable reaction vessel. The reaction can be initiated by gently heating the mixture, if desired. However, the saponification reaction of this invention will generally initiate spontaneously on stirring the reactants for a few minutes. When using carboxylic acid esters which are especially easily saponified (e.g., nitrophenyl esters) the reaction is self-initiating almost immediately and proceeds to substantially 100% completion in the matter of a few minutes, or less.

It is to be understood that the solutions of alkali metal hydroxides employed herein are not particularly miscible with the alkyl nitrile reaction medium. Apparently, some alkali metal hydroxide does partition into the alkyl nitrile and saponifies an equivalent amount of the organic acid ester, whereupon additional alkali metal hydroxide partitions into the alkyl nitrile, etc.

The nature of the alkali metal hydroxides employed herein is critical to securing the special advantages of this invention. Concentrated, aqueous solutions of lithium hydroxide and sodium hydroxide are useful herein, whereas aqueous solutions of potassium hydroxide, rubidium hydroxide and cesium hydroxide are not used in the practice of this invention, since the soaps prepared therefrom are rapidly and completely hydrated by the water which is present and are formed as tacky, viscous soap phases. Thus, the special advantages of the present process are lost when aqueous solutions of these latter three alkali metal hydroxides are used herein.

The solutions of sodium hydroxide and lithium hydroxide herein preferably comprise at least 30%, more preferably 50%, or greater, of the base. When using such concentrated solutions, the sodium or lithium carboxylate salts which are formed generally contain less than about 14% water, and are thus filterable, free-flowing solids which are easily separated from the reaction mixture. In most instances, with the more concentrated aqueous solutions of sodium hydroxide and lithium hydroxide (i.e., greater than about 50% solutions), the soaps which are formed contain from about 7% to about 10% water.

The nature of the fatty acid esters employed herein is not critical to the practice of this invention. Accordingly, the ester of any fatty acid or substituted fatty acid species with any alcohol or substituted alcohol species provides starting materials which can be used herein. It will be appreciated, of course, that some esters will react more rapidly than others. However, the present process has been found to be useful for saponifying even substantially inert esters such as the sucrose fatty octaesters, which demonstrates the exceptional efficacy of this reaction as a saponification process.

In the practice of this invention it is convenient to employ a stoichiometric amount of the sodium hydroxide or lithium hydroxide and ester to be saponified. For most purposes, an excess of the alkali metal hydroxide is employed to ensure that the reaction is carried to completion and that no ester is wasted. The alkyl nitrile is generally used in a solvent amount, i.e., sufficient to dissolve the acid ester. In some instances, the acid ester may not be entirely soluble in the alkyl nitrile and a ternary, heterogeneous reaction mixture of concentrated solution of alkali metal hydroxide/liquid alkyl nitrile/acid ester is formed. It does not appear to be necessary for the reaction mixture to be homogeneous, and excellent yields of the alkali metal salts of fatty acids are secured even under such conditions.

In an alternate mode, an excess of acid ester is used, and the mixture of any unreacted ester and alkyl nitrile is simply re-used with fresh, concentrated aqueous alkali metal hydroxide in subsequent processes. This avoids the need for any acid neutralization step to remove excess base during soap recovery. Thus, the soap recovery step involves simple filtration, followed by air drying to remove any entrained alkyl nitrile which may be present in the product.

It will be appreciated that small amounts (usually less than about 10% of the alkyl nitrile) of extraneous organic materials may contaminate the reaction systems used in any commercial scale soap making process. Excessive amounts of such extraneous materials may cause an undesirable dilution of the alkyl nitrile/alkali metal hydroxide base medium. Moreover, organic materials, such as extraneous solvents, which are miscible with the alkyl nitrile may solvate the alkali metal hydroxide and diminish the overall reactivity of the system. Thus, the presence of excessive amounts of extraneous organic materials is preferably avoided herein to assure that the special advantages of the process are obtained.

The saponification reaction of this invention is conveniently carried out at a weight ratio of organic acid ester:concentrated base:alkyl nitrile in the range of from about 1:0.1:1 to about 1:1:5, but other ratios can be used, as desired. "Super fatted" soaps can be prepared in standard fashion by using less than a stoichiometric amount of the alkali metal hydroxide with the ester.

The following examples illustrate the practice of this invention, but are not intended to be limiting thereof.

EXAMPLE I

Reaction of Triglycerides With Concentrated Sodium Hydroxide

To a mixture of 50 g. (0.067 mole) of a 50:50 mixture of tallow and coconut fats in 250 mls. of acetonitrile at a temperature of 75° C, is added 8.15 g. (0.20 mole) of sodium hydroxide dissolved in 8.15 g. of water. The reaction is initiated by gentle warming. Once initiated, the reaction mixture is maintained at reflux temperature, with stirring, for a total of five minutes. During this time, a layer of fine, white, solid powdered material forms in the reaction vessel.

The solid material is collected by filtration and air dried overnight (to remove acetonitrile solvent) to give a yield of ca. 90% of free-flowing sodium carboxylates (soaps) corresponding to the fatty acids in the starting material triglycerides.

In the process of Example I the acetonitrile is replaced by an equivalent amount of benzonitrile ($C_6H_5CN$) and essentially no reaction occurs.

In the process of Example I, the acetonitrile is replaced by an equivalent amount of propionitrile, butyronitrile, n-pentylnitrile, and cyclohexylnitrile, respectively, and equivalent results are secured. Saponification reactions carried out using the higher alkyl nitriles (greater than about $C_6$ alkyl) are much slower than with the preferred lower alkyl nitriles.

In the process of Example I, the concentrated (50%) aqueous solution of NaOH is replaced by an equivalent amount of a 50% aqueous solution of LiOH and a solid, filterable, free-flowing lithium soap is secured.

EXAMPLE II

Reaction of Tallow and Coconut Triglycerides with Potassium Hydroxide Solution

To a stirred mixture of 100 g. of 80% tallow-20% coconut triglycerides and 500 mls. of acetonitrile at 60° C is added 16.3 g. of a 50% aqueous solution of potassium hydroxide. The reaction mixture is stirred for three hours. Intermittent heating is used to maintain a reflux temperature (80° C–82° C).

The foregoing reaction mixture yields a tacky, hydrated, non-filterable mass of potassium "soaps" much like those obtained when using aqueous KOH solutions in ordinary "wet" soap making processes.

As can be seen from the foregoing, the soap making process of the present invention loses its special advantages of providing solid, filterable, free-flowing products when used to prepare soaps of alkali metals other than lithium or sodium.

EXAMPLE III

Preparation of Lithium Carboxylate

To a suspension of 50 g. (0.054 mole) of hydrogenated castor oil in 250 mls. of acetonitrile at 70° C is added 6.8 g. (0.162 mole) of lithium hydroxide monohydrate dissolved in 6.8 g. of water. The reaction mixture is stirred for 21 hours at reflux (81° C). The product which precipitates from solution is isolated by vacuum filtration of the hot reaction mixture and is solvent-stripped in a vacuum desiccator. The product is a solid, filterable lithium carboxylate, predominately 12-hydroxystearate, lithium salt.

EXAMPLE IV

Preparation of Bar Soap

The hydrated (ca. 7%–10% water) soap prepared in the manner of Example I herein is in a phase which is useful to form bar soaps in the ordinary manner, as follows.

| Ingredient | Wt. % |
|---|---|
| Soap (Na form)* | 89.75 |
| Coconut Oil Fatty Acids | 7.0 |
| Sodium Chloride | 1.0 |
| $TiO_2$ | 0.25 |
| Minors** | Balance |

*Prepared in the manner of Example I; ca. 10% water
**Perfume, coloring, perfume stabilizer A composition of the foregoing type is extruded through a standard soap making extruder and formed into bars, using commercial bar soap processing techniques. An excellent soap bar product which compares favorably with commercially available soaps is secured.

The slightly hydrated soaps prepared in the manner of this invention are in a convenient, free-flowing granular form and are particularly adapted for use in mechanical dispensers, such as those found in public lavatories.

EXAMPLE V

Saponification of Dimethyl Adipate 17.4 Grams (0.1 mole) of dimethyl adipate are dissolved in 100 mls. of acetonitrile and heated to 70° C. 8.2 Grams (0.2 mole) of sodium hydroxide dissolved in 6.0 g. of water are added to the reaction mixture. The reaction mixture is stirred at reflux temperature for 18 hours. The resulting solution is filtered hot and the solids are air dried to yield disodium adipate as the reaction product.

The foregoing illustrates that the process herein is useful for saponifying diacid esters.

What is claimed is:

1. A process for preparing the sodium or lithium salts of organic carboxylic acids which comprises saponifying the corresponding organic carboxylic acid ester with a concentrated aqueous solution of sodium hydroxide or lithium hydroxide in a liquid reaction medium comprising an alkyl nitrile, separating said salts from the reaction mixture, and removing excess alkyl nitrile from the salts.

2. A process according to claim 1 wherein the organic acid ester is a glyceride ester.

3. A process according to claim 2 wherein the glyceride ester is a tryglyceride.

4. A process according to claim 1 wherein the alkyl nitrile is a member selected from the group consisting of acetonitrile and propionitrile.

5. A process according to claim 1 for preparing lubricating greases comprising saponifying a $C_{10}$–$C_{24}$ organic acid ester with a concentrated aqueous solution of lithium hydroxide in an alkyl nitrile reaction medium.

6. A process according to claim 5 wherein the organic acid ester is a glyceride ester.

7. A process according to claim 6 wherein the glyceride ester is a triglyceride.

8. A process according to claim 5 wherein the alkyl nitrile is a member selected from the group consisting of acetonitrile and propionitrile.

9. A process according to claim 7 wherein the alkyl nitrile is acetonitrile and wherein the ester comprises the mixed glyceride esters derived from animal fats and oils or vegetable fats and oils.

10. A process according to claim 9 wherein the mixed glyceride esters comprise hydrogenated castor oil.

11. A process according to claim 1 for preparing soap comprising saponifying a $C_{10}-C_{20}$ organic acid ester with a concentrated aqueous solution of sodium hydroxide in an alkyl nitrile reaction medium.

12. A process according to claim 11 wherein the organic acid ester is a glyceride ester.

13. A process according to claim 12 wherein the glyceride ester is a triglyceride.

14. A process according to claim 11 wherein the alkyl nitrile is a member selected from the group consisting of acetonitrile and propionitrile.

15. A process according to claim 11 wherein the alkyl nitrile is acetonitrile and wherein the ester comprises the mixed glyceride esters derived from animal fats and oils or vegetable fats and oils.

* * * * *